United States Patent [19]

Fukuda et al.

[11] Patent Number: 5,576,365
[45] Date of Patent: Nov. 19, 1996

[54] PHOSPHORUS TYPE STABILIZER AND AN ORGANIC MATERIAL STABILIZED BY THE SAME

[75] Inventors: Kanako Fukuda; Tetsuo Yamaguchi; Shinya Tanaka, all of Osaka; Manji Sasaki, Hyogo, all of Japan

[73] Assignee: Sumitomo Chemical Company, Limited, Osaka, Japan

[21] Appl. No.: 444,951

[22] Filed: May 19, 1995

[30] Foreign Application Priority Data

May 25, 1994 [JP] Japan .................................. 6-111297
Feb. 28, 1995 [JP] Japan .................................. 7-039944

[51] Int. Cl.[6] .......................... C08K 5/527; C07F 9/6574
[52] U.S. Cl. ............................................... 524/117; 558/85
[58] Field of Search ................................ 558/85; 524/117

[56] References Cited

U.S. PATENT DOCUMENTS

| | | | |
|---|---|---|---|
| 4,252,750 | 2/1981 | Buysch et al. ................... | 524/117 X |
| 5,292,785 | 3/1994 | Pastor et al. ...................... | 524/117 |

FOREIGN PATENT DOCUMENTS

| | | |
|---|---|---|
| 0009115 | 4/1980 | European Pat. Off. . |
| 0569328 | 11/1993 | European Pat. Off. . |
| 6-321975 | 11/1994 | Japan . |
| 93/03839 | 3/1993 | WIPO . |

OTHER PUBLICATIONS

*Phosphorous and Sulfur*, 1984, vol. 19, pp. 1–10, Paul A. Odorisio et al., "Reaction of Seven–and Eight–Membered Cyclic Phosphorochloridites with Alkanolamines".

*Primary Examiner*—Johann Richter
*Assistant Examiner*—Michael G. Ambrose
*Attorney, Agent, or Firm*—Watson Cole Stevens Davis P.L.L.C.

[57] ABSTRACT

An organic phosphorus compound represented by the following formula (I):

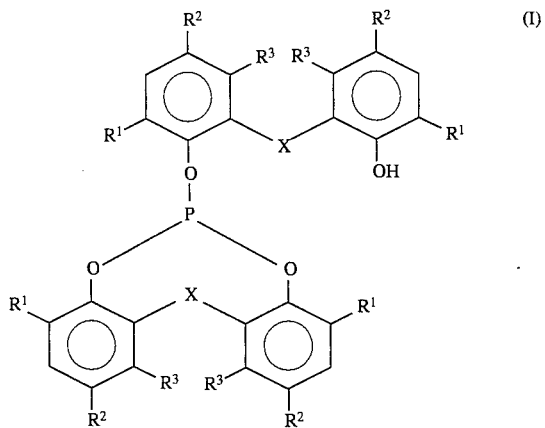

wherein $R^1$ and $R^2$ independently represent alkyl having 1–8 carbon atoms, cycloalkyl having 5–8 carbon atoms, alkylcycloalkyl having 6–12 carbon atoms, arylalkyl having 7–12 carbon atoms or phenyl; $R^3$ represents hydrogen or alkyl having 1–8 carbon atoms, X represents a direct bond or —CH($R^4$)— wherein $R^4$ represents hydrogen or alkyl having 1–8 carbon atoms; a phosphorus type stabilizer for various organic materials such as synthetic resins or synthetic rubbers or an organic material composition comprising the same.

6 Claims, No Drawings

PHOSPHORUS TYPE STABILIZER AND AN ORGANIC MATERIAL STABILIZED BY THE SAME

FIELD OF THE INVENTION

The present invention relates to an organic phosphorus compound, a phosphorus type stabilizer and organic materials stabilized by the same.

BACKGROUND OF THE INVENTION

Organic materials such as thermoplastic resins, thermosetting resins, natural rubbers, synthetic rubbers, mineral oils, lubricants, adhesives and paints are deteriorated, together with depolymerization and crosslinking, by the action of heat, oxygen, etc. during their production, processing or use. Due to the deterioration, their merchandize values are markedly lowered. In order to prevent the deterioration, i.e. thermal degradation, thermal oxidative degradation or the like, various phenol type antioxidants, phosphorus type antioxidants or the like have been added to organic materials. Among them, phosphorus type antioxidants such as phosphite compounds or phosphonite compounds have been widely used as processing stabilizers which cope with high temperature and high shear in processing steps of synthetic resins or synthetic rubber, because they are superior in retaining melt flow rates of synthetic resins or synthetic rubber and in preventing their heat-discoloration.

Typical examples of the phosphorus type antioxidants include Distearyl pentaerythritol diphosphite, Tris(2,4-di-t-butylphenyl)phosphite, Bis(2,4-di-t-butylphenyl) pentaerythritol diphosphite, Tetrakis(2,4-di-t-butylphenyl) 4,4'-biphenylene diphosphite and Bis(2,6-di-t-butyl-4-methylphenyl) pentaerythritol diphosphite However, these usual phosphorus type antioxidants are not, satisfactory enough in stabilizing effects for preventing thermal degradation and thermal oxidative degradation and more improved antioxidants have been desired. For example, though Bis(2,4-di-t-butylphenyl) pentaerythritol diphosphite imparts excellent processing stability at high temperature, it is easily hydrolyzed and loses its processing stability effect. As a result of its hydrolysis during storage, it cannot stabilize organic materials any more. It also has a problem that it erodes processing apparatuses because of phosphorous acid, etc. produced by its hydrolysis. Tris(2,4-di-t-butylphenyl) phosphite, though excellent in hydrolysis resistance, its processing stabilizing effect is not satisfactory enough.

Particularly in the fields of synthetic resins, since processing temperature has been getting higher recently in order to improve their productivity, processing stabilizers excellent in resistance to hydrolysis and imparting high processing stability have processing become desired more earnestly.

SUMMARY OF THE INVENTION

An object of the present invention is to provide an organic phosphorus compound which can be used as a phosphorus type stabilizer for organic materials.

Another object of the present invention is to provide a phosphorus type stabilizer for organic materials comprising the organic phosphorus compound, which imparts high stabilizing effect by preventing thermal degradation and thermal oxidation of synthetic resin and synthetic rubber, particularly in processing steps, and is resistant to hydrolysis.

Further object of the present invention is to provide a method for stabilizing organic materials by adding the phosphorus type stabilizer to the organic materials.

Still further object of the present invention is to provide an organic material composition stabilized by the phosphorus type stabilizer.

The inventors of the present invention have found that an organic phosphorus compound having a specific chemical structure is very effective for stabilizing organic materials and have accomplished the present invention.

DESCRIPTION OF THE INVENTION

Thus, the present invention provides an organic phosphorus compound represented by the following formula (I):

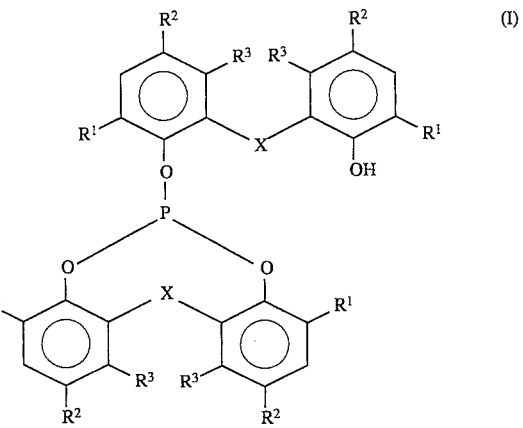

wherein $R^1$ and $R^2$, which are same or different, independently represent an alkyl group having 1–8 carbon atoms, a cycloalkyl group having 5–8 carbon atoms, an alkylcycloalkyl group. having 6–12 carbon atoms, an arylalkyl group having 7–12 carbon atoms or a phenyl group; $R^3$ represents hydrogen or an alkyl group having 1–8 carbon atoms, X represents a direct bond or —CH($R^4$)— wherein $R^4$ represents hydrogen or an alkyl group having 1–8 carbon atoms.

The present invention also provides a phosphorus type stabilizer comprising the organic phosphorus compound of formula (I).

The present invention further provides a method for stabilizing an organic material by adding the phosphorus type stabilizer to the organic material.

The present invention still further provides an organic material composition which comprises an organic material and the organic phosphorus compound of formula (I).

Examples of the alkyl group denoted by $R^1$ or $R^2$ in formula (I) include methyl, ethyl, propyl, isopropyl, n-butyl, sec-butyl, t-butyl, t-pentyl, n-octyl, t-octyl, 2-ethylhexyl and isooctyl. Examples of the cycloalkyl group denoted by $R^1$ or $R^2$ in formula(I) include cyclopentyl and cyclohexyl. Examples of the alkylcycloalkyl group denoted by $R^1$ or $R^2$ in formula(I) include 1-methylcyclohexyl and 1-methyl-4-isopropylcyclohexyl. Examples of the arylalkyl group denoted by $R^1$ or $R^2$ in formula (I) include benzyl, α-methylbenzyl and α, α-dimethylbenzyl. As R' in formula (I), an alkyl group which has 4–8 carbon atoms and in which at least one of the carbon atoms is a quaternary carbon atom, such as t-butyl, t-pentyl or t-octyl, is preferred and particularly preferred is t-butyl. As $R^2$ in formula (I), an alkyl group having 1–5 carbon atoms such as methyl, ethyl, n-propyl, isopropyl, t-butyl or t-pentyl is preferred.

Examples of the alkyl group denoted by $R^3$ in formula (I) include methyl, ethyl, n-propyl, iso-propyl, n-butyl, sec-butyl, t-butyl, n-pentyl, t-pentyl, n-octyl, t-octyl and isooctyl. As $R^3$ in formula (I), a hydrogen atom or a alkyl group having 1–4 carbon atoms is preferred and particularly preferred is a hydrogen atom or methyl.

Examples of the alkyl group denoted by $R^4$ include methyl, ethyl, iso-propyl, n-propyl, n-butyl, t-butyl, sec-butyl, n-pentyl, t-pentyl, n-octyl, t-octyl and isooctyl. As $R^4$, a hydrogen atom or an alkyl group having 1–4 carbon atoms is preferred and particularly preferred is s hydrogen atom or methyl.

The organic phosphorus compound of formula (I) can be produced, for example, by reacting a bisphenol compound represented by the following formula (II):

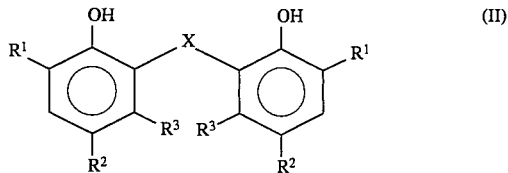

wherein $R^1$, $R^2$, $R^3$ and X are as defined above, with phosphorus trihalide in the presence of an organic base.

The bisphenol compound represented by the formula(II) is a known compound and is on the market. The compound as on the market can be used for the production of the organic phosphorus compound of formula(I).

The organic phosphorus compound of formula (I) wherein X is —$CH(R^4)$— can also be produced by reacting an alkylphenol and an aldehyde according to a known method, such as a method mentioned in U.S. Pat. No. 2,538,355 or JP-A-52-122350. The organic phosphorus compound of formula (I) wherein X is a direct bond can also be produced by a condensation reaction of an alkylphenol according to a known method, such as a method mentioned in U.S. Pat. No. 4,380,676 (=JP-B-2-47451).

Examples of phosphorus trihalide used for the reaction with the bisphenol compound of formula(II) include phosphorus trichloride and phosphorus tribromide. Among them, phosphorus trichloride is preferred.

Example of the organic base used in the reaction of phosphorus trihalide with the bisphenol compound of formula (II) include pyridines and amines. Examples of the pyridines include pyridine and picoline. Among them, pyridine is preferred. Amines used as the organic base may be primary, secondary or tertiary amines. Examples of the amines include t-butylamine, t-pentylamine, t-hexylamine, t-octylamine, dimethylamine, diethylamine, di-t-butylamine, di-t-pentylamine, di-t-hexylamine, di-t-octylamine, trimethylamine, triethylamine, N,N-dimethylaniline and N,N-diethylaniline. Among them, triethylamine is preferred.

The reaction of phosphorus trihalide with the bisphenol compound of formula (II) is usually carried out in an organic solvent. Examples of the organic solvent used for the reaction include aromatic hydrocarbons such as benzene, toluene, xylene or the like; aliphatic hydrocarbons such as n-hexane, n-heptane, n-octane or the like; oxygen-containing hydrocarbons such as diethylether, tetrahydrofuran, or the like; and halogenated hydrocarbons such as chloroform, carbon tetrachloride, monochlorobenzene, dichlorobenzene or the like. Among them, toluene is preferred.

Usually, the reaction is carried out in two steps. In the first step, phosphorus trihalide and a part of the bisphenol compound of formula (II) are reacted. In the second step, remaining bisphenol compound of formula (II) is added to the reaction mixture obtained in the first step and, then, the reaction is further carried out.

In the first step, the phosphorus trihalide is preferably used in an amount of 0.9–1.1 mole, particularly preferred 0.95–1.05 mole, per mole of the bisphenol compound. In the first step, the organic base is preferably used in an amount of 2–2.4 moles, particularly preferred 2–2.1 moles, per 1 mole of the phosphorus trihalide. The first step is usually carried out at a temperature of 0°–150° C. for 2–3 hours in an organic solvent. The first step can be carried out either under an atmospheric pressure or under an elevated pressure.

The intermediate produced in the first step is a halogenophosphite represented by the following formula (III):

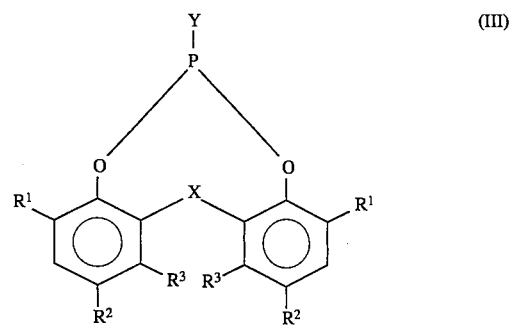

wherein $R^1$, $R^2$, $R^3$ and X are as defined above and Y represents a halogen atom.

The intermediate represented by the formula (III) may be isolated from the reaction mixture obtained in the first step to be used for the second step. However, usually, the reaction mixture obtained in the first step is used for the second step as it is (=without any isolation).

The bisphenol compound added in the second step is preferably the same as the bisphenol compound added in the first step and the amount of bisphenol compound added in the second step is preferably –1.1 mole, more preferably 1–1.05 mole per mole of the bisphenol compound added in the first step.

In the second step, the organic solvent used in the first step can be used as it is. It is preferred that the organic base is also added in the second step. The amount of the organic base to be added in the second step is preferably 1–1.2 mole, more preferably 1–1.05 mole, per 1 mole of bisphenol compound added in the second step. If the amount of the organic base exceeds 2 moles per of the phosphorus trihalide, it is preferred that the organic base of the excess amount i.e. exceeding 2 moles is added in the second step. The second step is usually carried out at a temperature of 0°–120° C. for 4–5 hours.

After completion of the reaction (the second step) halogenated hydroacid salt produced in the reaction and the solvent are removed and, then, crystallization is carried out by using a hydrocarbon solvent such as hexane to obtain a organic phosphorus compound of formula (I).

The organic phosphorus compound of Formula (I) is resistant to hydrolysis ad is effective for stabilizing the organic materials by preventing thermal degradation and thermal oxidative degradation of the organic materials.

Examples of the organic materials which can be stabilized by the organic phosphorus compound of formula(I) include synthetic resins, synthetic or natural rubbers, paints, waxes and lubricating oils. Examples of the synthetic resins include polyethylene, such as high density polyethylene (HD-PE), low density polyethylene (LD-PE) or linear low density polyethylene; polypropylene; methylpentene polymer;

copolymer of ethylene and ethylacrylate (EEA resin); copolymer of ethylene and vinylacetate; copolymer of ethylene and vinylalcohol; polystyrenes such as polystyrene, poly(p-methylstyrene) or poly(α-methylstyrene); copolymer of acrylonitrile and styrene (AS resin); copolymer of acrylonitrile, butadiene and styrene (ABS resin); copolymer of special acryl rubber, acrylonitrile and styrene (AAS resin); copolymer of acrylonitrile, chlorinated ethylene and styrene (ACS resin); chlorinated polyethylene; polychloroprene; chlorinated rubber; polyvinylchloride; polyvinylidene chloride; methacryl resin; fluorocarbon resin; polyacetal; grafted polyphenyleneether resin; polyphenylenesulfide resin; polyurethane; polyamide; polyethyleneterephthalate; polybutyleneterephthalate; polycarbonate; polyacrylate; polysulfone; polyetheretherketone; polyethersulfone: aromaticpolyester resin; epoxy resin; diallylphthalate prepolymer; silicone resin; unsaturated polyester resin; acrylated benzoguanamine resin; benzoguanamine melamine resin and urea resin. Examples of the synthetic or natural rubbers include polybutadiene, 1,2-polybutadiene, polyisoprene; copolymer of styrene and butadiene; copolymer of butadiene and acrylonitrile; copolymer of ethylene and propylene; silicone rubber; epichlorohydrin rubber; acryl rubber and natural rubber. Examples of the paints include chlorine rubber paint, polyester resin paint, urethane rein paint, epoxy resin paint, acryl resin paint, vinyl resin paint, aminoalkyd resin paint, nitrocellulose resin paint and oil paint. Among the organic materials mentioned above, synthetic resins such as polyolefin and synthetic rubbers such as polybutadiene are more effectively stabilized by the organic phosphorus compound of formula (I). Polyolefin such as polyethylene and polypropylene are particularly effectively stabilized.

The organic material to be stabilized not an organic isocyanate or polyisocyanate.

The organic phosphorus compound of formula (I) is mixed woth the organic materials to be stabilized. Amount of the organic phosphorus compound of formula (I) is usually 0.01 part by weight or more, preferably 0.01–2 parts by weight, per 100 parts by weight of the organic materials. If the amount is less than 0.01 part by weight, stabilizing effect is not satisfactory. If the amount exceeds 2 parts by weight, the effect does not increase in proportion to the increased amount of the organic phosphorus compound, therefore increasing the amount beyond 2 parts by weight is economically disadvantageous.

The organic material composition comprising the organic phosphorus compound of formula (I) according to the present invention may further comprise other additives such as phenolic antioxidants, sulfur type containing antioxidants, phosphorus containing antioxidants other than the organic phosphorus compound of formula (I), ultraviolet absorbers, hindered amine type light stabilizers, lubricants, plasticizers, fire retardants, nucleating agents, metal deactivators, antistatic agents, pigments, inorganic fillers, or the like, if desired. These additives can be added together with the organic phosphorus compound of formula (I) or can be added in a different step, Among the additives other than the organic phosphorus compound of formula (I), phenolic antioxidants are preferred.

Any known methods and any known apparatuses which have been used for producing a homogenized mixture can be used for mixing the organic phosphorus compound of formula(I) and other optional additives with organic materials. For example, when the organic material is a solid polymer, the organic phosphorus compound and other additives may be directly dry-blended with the solid organic material or they may be blended with the solid organic materials in the form of a master batch. When the organic material is a synthetic polymer, the organic phosphorus compound and other additives may be blended with a solution or suspension of the synthetic polymer during polymerization of the synthetic polymer or after completion of the polymerization.

When the organic material is a liquid such as oil, the organic phosphorus compound and other additives may be added directly to the organic material and dissolved into the organic material, or they may be added to the organic material in the form of solution or suspension in a liquid medium.

EXAMPLE

The present invention will be explained in more detail with reference to following examples. The examples should not be construed to limit the present invention. In the examples, "%" and "part" are by weight unless otherwise mentioned.

Synthesis Example 1

Synthesis of "2-[2-(4,8-di-t-butyl-2,10-dimethyl-12H-dibenzo[d,g][1,3,2]dioxaphosphosin-6-yl]oxi-3-t-butyl-5-methylbenzyl]-6-t-butyl-4-methylphenol (hereinafter referred to as Compound 1)"

Into a 500 ml four-necked flask equipped with a thermometer, a stirrer and a condenser, 31 g of 2,2'-methylenebis(6-t-butyl-4-methylphenol), 100 ml of toluene and 9.2 g of triethylamine were charged and the inside of the flask was replaced with nitrogen gas. Then, while stirring, 12.5 g of phosphorus trichloride was dropwise added. After completion of the dropwise addition, the reaction mixture was kept at 80° C. for 3 hours and 9.6 g of triethylamine and 31 g of 2,2'-methylenebis(6-t-butyl-4methylphenol) which had been dissolved in 100 ml of toluene were added thereto, and the resulting reaction mixture was kept under refluxing for 6 hours, Thereafter, the reaction mixture was cooled to room temperature and hydrochloric acid salt of triethylamine produced in the reaction was filtered off. The filtrate was concentrated and the residue was crystallized by hexane to obtain 47.1 g of white crystalline product (Compound 1).
Mass analysis (FD-MS): m/z 708
Elemental analysis: P:4.7%

(Theoretical value=calculated as $C_{46}H_{61}O_4P$: P: 4.4%)
Melting point: 197°–200° C.

Synthesis Example 2

Synthesis of
"2-[2-(2,4,8,10-tetra-t-butyl-12H-dibenzo[d,g][1,3,2] dioxaphosphosin-6-yl)oxi-3,5-di-t-butylbenzyl]-4,6-di-t-butylphenol (hereinafter referred to as Compound 2)"

Synthesis example 1 was repeated, except that 31 g of 2,2'-methylenebis(6t-butyl-4-methylphenol) was replaced by 38.6 g of 2,2'-methylenebis(4,6-di-t-butylphenol) to obtain 69.7 g of white crystalline product (Compound 2).
Mass analysis (FD-MS): m/z 867
Elemental analysis: P: 3.6%

(Theoretical value=calculated as $C_{58}H_{85}O_4P$: P: 3.5%)
Melting point: 254°–256° C.

Synthesis Example 3

Synthesis of "2-[1-{2-(4,8-di-t-butyl-2,10-dimethyl-12-methyl-12H-dibenzo[d,g][1,3,2]dioxaphosphosin-6-yl)oxi-3-t-butyl-5-methylphenyl}ethyl]-6-t-butyl-4-methylphenol (hereinafter referred to as Compound 3)"

Synthesis example 1 was repeated, except that 31 g of 2,2'-methylenebis(6-t-butyl-4methylphenol) was replaced by 32.1 g of 2,2'-ethylidenebis(6-t-butyl--methylphenol) to obtain 46.5 g of white crystalline product (Compound 3).
Mass analysis (FD-MS): m/z 737
Elemental analysis: P: 4.0%
(Theoretical value=calculated as $C_{48}H_{65}O_4P$: P: 4.2%)
Melting point: 284°–286° C.

SYNTHESIS EXAMPLE 4

Synthesis of "2-[1-{2-(2,4,8,10-tetra-t-butyl-12-methyl-12H-dibenzo[d,g][1,3,2]dioxaphosphosin-6-yl)oxi-3,5-di-t-butylphenyl}ethyl]-4,6-di-t-butylphenol (hereinafter referred to as Compound 4)"

Synthesis example 1 was repeated, except that 31 g of 2,2'-methylenebis(6-t-butyl-4-methylphenol) was replaced by 39.9 g of 2,2'-ethylidenebis(4,6-di-t-butylphenol) to obtain 67.8 g of white crystalline product (Compound 4).
Mass analysis (FD-MS): m/z 904
Elemental analysis: P: 3.3%
(Theoretical value=calculated as $C_{60}H_{89}O_4P$: P: 3.4%)
Melting point: 198°–201° C.

Each of the organic phosphorus compounds obtained in synthesis example 1–4 were mixed with an organic material according to the formulation shown in following Application examples for their evaluation. In the Application examples, each of following compounds were also mixed with an organic material for comparison.
P-1: Bis(2,4-di-t-butylphenyl)pentaerithritol diphosphite
P-2: Tris(2,4-di-t-butylphenyl)phosphite

Application Example 1

Thermal Stability Test of Polypropylene

| [Formulation of the composition] | |
|---|---|
| Unstabilized polypropylene | 100 parts |
| Calcium stearate | 0.05 part |
| AO–1* | 0.05 part |
| Test sample (shown in Table 1) | 0.1 part |

*AO–1 : tetrakis[methylene-3-(3,5-di-t-butyl-4-hydroxyphenyl)propionate]methane

The above-described composition was mixed with melting at 230° C. by using a single screw extruder of 30 mm bore diameter to obtain a pelletized composition. The pellets thus obtained were put into a melt-indexer and melt flow rate of the composition (g/10 minutes) after 5 minutes of resistance was measured at 250° C. according to JIS K 7210. Lower melt flow rate after 5 minutes of resistance means superior processing stability. The results are shown in Table 1.

The test samples were left for 7 days in a thermostat kept at a temperature of 40° C. at a relative humidity of 80% to accelerate hydrolysis. Thereafter, hydrolysis resistance of these treated test samples were evaluated by conducting same tests as above-mentioned. Higher processing stability after the treatment under 40° C. 80% indicates superior hydrolysis resistance. The results are also shown in Table 1.

TABLE 1

| Run No. (Test sample) | Present invention | | | | Comparison | | |
|---|---|---|---|---|---|---|---|
| | 1 | 2 | 3 | 4 | 5 | 6 | 7 |
| | (Amount of the Test sample "part") | | | | | | |
| Compound 1 | 0.1 | — | — | — | — | — | — |
| Compound 2 | — | 0.1 | — | — | — | — | — |
| Compound 3 | — | — | 0.1 | — | — | — | — |
| Compound 4 | — | — | — | 0.1 | — | — | — |
| P-1 | — | — | — | — | — | 0.1 | — |
| P-2 | — | — | — | — | — | — | 0.1 |
| Melt Flow rate (g/10 minutes) | | | | | | | |
| before-hydrolysis | 22.9 | 25.0 | 26.2 | 30.2 | 33.1 | 21.5 | 32.5 |
| after-hydrolysis | 22.8 | 25.2 | 26.1 | 30.0 | — | 32.5 | 32.3 |

Application Example 2

Thermal Stability Test of Linear Low Density Polyethylene

| [Formulation of the compounded composition] | |
|---|---|
| Unstabilized linear low density polyethylene | 100 parts |
| Calcium stearate | 0.1 part |
| AO–2* | 0.05 part |
| Test sample (shown in Table 2) | 0.05 or 0.1 part |

*AO–2 : n-octadecyl 3-(3,5-di-t-butyl-4-hydroxyphenyl) propionate

The above-described compounded composition was mixed with melting at 230° C. by using a single screw extruder of 30 mm bore diameter to obtain a pelletized composition. The pellets thus obtained were put into a melt-indexer and melt flow rate of the composition (g/10 minutes) after 15 minutes of resistance was measured at 250° C. according to JIS K 7210 and thermal stability of the composition was evaluated. Higher melt flow rate after 15 minutes of resistance means superior processing stability. The results are shown in Table 2.

The test samples were left for 7 days in a thermostat kept at a temperature of 0° C. at a relative humidity of 80% to accelerate hydrolysis. Thereafter, hydrolysis resistance of these treated test samples were evaluated by conducting same tests as above-mentioned. The results are also shown in Table 2.

TABLE 2-1

| Run No. (Test sample) | Present invention | | | | | | | |
|---|---|---|---|---|---|---|---|---|
| | 1 | 2 | 3 | 4 | 5 | 6 | 7 | 8 |
| | (Amount of the Test samp "part") | | | | | | | |
| Compound 1 | 0.05 | — | — | — | 0.1 | — | — | — |
| Compound 2 | — | 0.05 | — | — | — | 0.1 | — | — |
| Compound 3 | — | — | 0.05 | — | — | — | 0.1 | — |
| Compound 4 | — | — | — | 0.05 | — | — | — | 0.1 |
| P-1 | — | — | — | — | — | — | — | — |
| P-2 | — | — | — | — | — | — | — | — |
| Melt Flow rate (g/10 minutes) | | | | | | | | |
| before-hydrolysis | 6.1 | 6.1 | 5.7 | 5.3 | 7.0 | 6.5 | 6.5 | 6.4 |
| after-hydrolysis | 6.1 | 6.3 | 5.9 | 5.4 | 6.9 | 6.4 | 6.3 | 6.4 |

TABLE 2-2

|  | Comparison | | |
| --- | --- | --- | --- |
| Run No. | 9 | 10 | 11 |
| (Test sample) | (Amount of the Test sample "part") | | |
| Compound 1 | — | — | — |
| Compound 2 | — | — | — |
| Compound 3 | — | — | — |
| Compound 4 | — | — | — |
| P-1 | — | 0.05 | — |
| P-2 | — | — | 0.05 |
| Melt Flow rate (g/10 minutes) | | | |
| before-hydrolysis | 4.7 | 6.4 | 5.1 |
| after-hydrolysis | — | 4.7 | 5.1 |

Organic phosphorus compounds of the present invention exhibit excellent properties as stabilizers for various organic materials such as synthetic resins or synthetic rubbers. Since the organic phosphorus compounds of the present invention are resistant to hydrolysis, they can be stored for long period and impart high stabilizing effects to the organic materials regardless of environments to which they have been exposed after their production. Synthetic resins mixed with the organic phosphorus compounds are stable against thermal degradation and thermal oxidative degradation during their production, processing and use.

What we claim is:

1. A composition comprising an organic material and an organic phosphorus compound represented by the following formula (I):

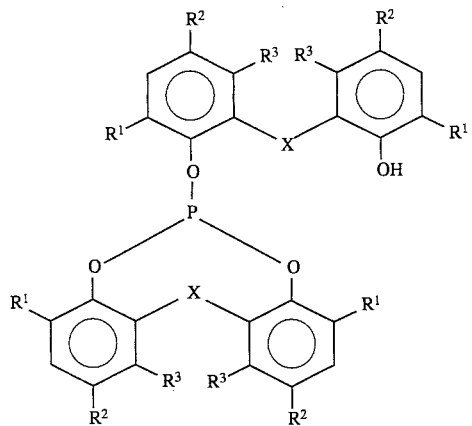

(I)

wherein $R^1$ and $R^2$, which are same or different, independently represent an alkyl group having 1–8 carbon atoms, a cycloalkyl group having 5–8 carbon atoms, an alkylcycloalkyl group having 6–12 carbon atoms, an arylalkyl group having 7–12 carbon atoms or a phenyl group; $R^3$ represents hydrogen or an alkyl group having 1–8 carbon atoms, X represents a direct bond or —$CH(R^4)$— wherein $R^4$ represents hydrogen or an alkyl group having 1–8 carbon atoms, wherein the amount of the organic phosphorus compound is 0.01 part by weight or more per 100 parts by weight of the organic material.

2. A composition according to claim 1 wherein the organic material is a synthetic resin or a synthetic rubber.

3. A composition according to claim 1 wherein the organic material is a polyolefin.

4. A composition according to claim 1 wherein the amount of the organic phosphorus compound is 0.01–2 parts by weight per 100 parts by weight of the organic material.

5. The composition of claim 1 further including an antioxidant.

6. A method for stabilizing an organic material which comprises adding an organic phosphorus compound represented by the following formula (I):

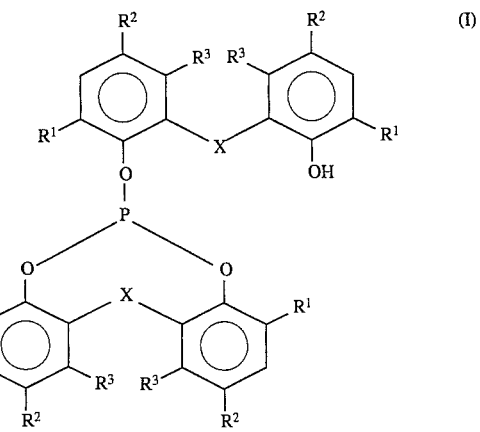

(I)

wherein $R^1$ and $R^2$, which are same or different, independently represent an alkyl group having 1–8 carbon atoms, a cycloalkyl group having 5–8 carbon atoms, an alkylcycloalkyl group having 6–12 carbon atoms, an arylalkyl group having 7–12 carbon atoms or a phenyl group; $R^3$ represents hydrogen or an alkyl group having 1–8 carbon atoms, X represents a direct bond or —$CH(R^4)$— wherein $R^4$ represents hydrogen or an alkyl group having 1–8 carbon atoms, to an organic material.

* * * * *